United States Patent
Srivastava et al.

(10) Patent No.: US 9,631,216 B2
(45) Date of Patent: Apr. 25, 2017

(54) METHOD FOR REDUCING HETEROGENEITY OF ANTIBODIES AND A PROCESS OF PRODUCING THE ANTIBODIES THEREOF

(75) Inventors: Ruchika Srivastava, Bangalore (IN); Sneha Lakshmandas Hemdev, Bangalore (IN); Ankur Bhatnagar, Bangalore (IN); Saravanan Desan, Bangalore (IN); Anuj Goel, Bangalore (IN); Harish Iyer, Bangalore (IN)

(73) Assignee: Biocon Research Limited, Karnataka (IN)

( * ) Notice: Subject to any disclaimer, the term of this patent is extended or adjusted under 35 U.S.C. 154(b) by 246 days.

(21) Appl. No.: 14/114,639

(22) PCT Filed: Apr. 27, 2012

(86) PCT No.: PCT/IB2012/052114
§ 371 (c)(1),
(2), (4) Date: Feb. 12, 2014

(87) PCT Pub. No.: WO2012/147053
PCT Pub. Date: Nov. 1, 2012

(65) Prior Publication Data
US 2014/0199729 A1    Jul. 17, 2014

(30) Foreign Application Priority Data
Apr. 29, 2011  (IN) ............... 1483/CHE/2011

(51) Int. Cl.
| | |
|---|---|
| *C12N 5/10* | (2006.01) |
| *C12N 5/00* | (2006.01) |
| *C12N 5/18* | (2006.01) |
| *C12P 21/00* | (2006.01) |
| *A61K 39/395* | (2006.01) |
| *C07K 16/00* | (2006.01) |

(52) U.S. Cl.
CPC ........ *C12P 21/00* (2013.01); *A61K 39/39591* (2013.01); *C07K 16/00* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 5,126,250 A | 6/1992 | McDonough et al. | |
| 6,048,728 A * | 4/2000 | Inlow | C12N 5/005 435/325 |
| 7,709,229 B2 * | 5/2010 | Casatorres Hernandez | C07K 14/61 435/325 |
| 8,440,458 B2 * | 5/2013 | Zijlstra | C12N 5/0603 435/289.1 |
| 8,809,049 B2 * | 8/2014 | Prentice | C12N 5/0031 435/325 |
| 2010/0297697 A1 | 11/2010 | Ambrosius et al. | |

FOREIGN PATENT DOCUMENTS

| | | | |
|---|---|---|---|
| WO | WO02101019 | * | 12/2002 |
| WO | 2006047340 A2 | | 5/2006 |
| WO | 2009027471 A1 | | 3/2009 |
| WO | WO 2009114641 | * | 3/2009 |
| WO | WO2010017338 | * | 2/2010 |
| WO | 2010125187 A2 | | 11/2010 |

* cited by examiner

*Primary Examiner* — Michail Belyavskyi
(74) *Attorney, Agent, or Firm* — Schwegman Lundberg & Woessner, P.A.

(57) ABSTRACT

The present disclosure relates to a method of reducing heterogeneity in antibodies during culturing, wherein the heterogeneity is due to proportion of charge variant of the antibody. The disclosure also comprises a process of growing cells in a cell culture system that results in antibodies with the reduced heterogeneity. In one embodiment antibody heterogeneity is reduced by the addition of divalent transitional metal ions such as zinc ($Zn^{2+}$) to the cell culture medium. In another embodiment antibody heterogeneity is reduced by decreasing the osmolality of the cell culture medium.

19 Claims, 7 Drawing Sheets

METHOD FOR REDUCING HETEROGENEITY OF ANTIBODIES AND A PROCESS OF PRODUCING THE ANTIBODIES THEREOF

TECHNICAL FIELD

The present disclosure relates to methods of improving protein production, e.g., large-scale commercial protein production such as antibody production, utilizing a modified cell culture method comprising a cell growth phase and a polypeptide production phase. The modified cell culture method controls process attributes and operating parameters to achieve polypeptide products that have altered charge variants/basic variants. The present disclosure is directed towards reducing heterogeneity in antibodies. More specifically the disclosure comprises method of growing cells in a cell culture system that decreases heterogeneity among charge variants by decreasing the proportion of basic variants.

BACKGROUND AND PRIOR ART OF THE DISCLOSURE

A large proportion of biotechnology products, whether commercially available or in development, are protein therapeutics. There is hence a large and increasing demand for production of proteins in cell cultures, e.g., in animal cell cultures, and for improved methods related to such production. Thus, a significant quantity of research focuses on animal cell culture conditions and methods that can optimize the polypeptide output, i.e., conditions and methods that support high cell density and high titer of protein.

The C-terminal lysine variation is commonly observed in biopharmaceutical monoclonal antibodies. Monoclonal antibody heterogeneity can be attributed to various factors such as amino terminal modifications (e.g., to pyroglutamate), incomplete processing of the C-terminus, asparagine deamidation, phosphorylation, glycosylation, oxidation, mutations etc. These kinds of variations occur in many type of proteins and can impact their activity and stability in biotherapeutics. Homogeneity of antibodies is an important attribute and is regarded as essential for demonstrating safety and efficacy of drugs as required by FDA and other regulatory agencies.

Recombinant monoclonal antibodies have been shown to have C-terminal heterogeneity with either an arginine (Arg) or lysine (lys) at the C-terminus. When these C-terminal variants of MAbs are treated with Carboxypeptidase B, an exopeptidase, Arg and Lys are cleaved from the C-terminus of both the antibody subunits, eliminating C-terminal heterogeneity.

Carboxypeptidases (CPs) are enzymes that catalyze the hydrolysis of the C-terminal peptide bond in peptides and proteins. The removal of one or a few amino acids from the C-terminus of a peptide or protein can have profound effects on the biological activity of that molecule. Heterogeneity of MAb is common due to the various modifications introduced over the lifespan of the molecules from the point of synthesis to the point of complete clearance from the subject. It is important to study the modifications of a therapeutic as there is a possibility of it affecting the activity/safety of the preparation leading to loss of efficacy and risk of adverse side effects.

U.S. Pat. No. 5,126,250 discloses a method of reducing the heterogeneity of secreted antibodies from antibody-producing cells.

STATEMENT OF THE DISCLOSURE

Accordingly, the present disclosure relates to a method of reducing heterogeneity in antibodies obtained by cell culturing, said method comprises adding divalent transitional metal ions to the antibody producing culture medium or altering osmolality of the culture medium or a combination thereof to obtain said antibodies with reduced heterogeneity; and a process for producing antibody having reduced heterogeneity, said process comprising acts of: (a) culturing cells in culture medium for producing the antibody, and adding divalent transitional metal ions to the culture medium or altering osmolality of the culture medium or a combination thereof, and (b) recovering the antibody from the culture medium having the reduced heterogeneity.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where.

NOTE: In Control, no Zinc ions have been fed.

DETAILED DESCRIPTION OF THE DISCLOSURE

The present disclosure relates to a method of reducing heterogeneity in antibodies obtained by cell culturing, said method comprises act of adding metal ions to the antibody producing culture medium or altering osmolality of the culture medium or a combination thereof to obtain said antibodies with reduced heterogeneity.

In an embodiment of the present disclosure, the heterogeneity is due to proportion of charge variant of the antibody; and wherein the reduction in the heterogeneity is carried out by reducing the proportion of Lysine residue on C-terminal of the antibody.

In another embodiment of the present disclosure, the heterogeneity is reduced by carrying out the said method for proportion of antibodies ranging from about 75% to about 100%.

In yet another embodiment of the present disclosure, the antibody is a naturally occurring antibody or a recombinant antibody selected from a group comprising monoclonal antibody, modified antibody, derivative of antibody and fragment of antibody or any combination thereof.

In still another embodiment of the present disclosure, the heterogeneity is reduced by decreasing basic variant proportion of the antibody from about 3% to about 30% and increasing main peak/0 Lysine from about 5% to about 25%.

In still another embodiment of the present disclosure, the divalent transitional metal ion is $Zn^{+2}$, at a concentration ranging from about 0.05 mM to about 1.5 mM.

In still another embodiment of the present disclosure, the osmolality of the culture medium is altered to provide osmolality ranging from about 240 mOsm/Kg to about 260 mOsm/Kg.

In still another embodiment of the present disclosure, the culturing is fed batch culturing; and comprises mammalian cell culturing, preferably chinese hamster ovary (CHO) cell line culturing.

In still another embodiment of the present disclosure, the addition of metal ions is carried out firstly during cell growth phase and secondly during polypeptide production phase of the cell culturing; or wherein the addition of the metal ion is carried out at an initial phase before said culturing of the cells.

The present disclosure further relates to a process for producing antibody having reduced heterogeneity, said process comprising acts of: (a) culturing cells in culture medium for producing the antibody, and adding divalent transitional metal ions to the culture medium or altering osmolality of the culture medium or a combination thereof, and (b) recovering the antibody from the culture medium having the reduced heterogeneity.

In an embodiment of the present disclosure, the cells are cultured at a concentration ranging from about $0.5 \times 10^6$ cells/ml to about $0.6 \times 10^6$ cells/ml.

In another embodiment of the present disclosure, the culturing is carried out at temperatures ranging from about 36° C. to about 38° C.

In yet another embodiment of the present disclosure, the antibody is a naturally occurring antibody or a recombinant antibody selected from a group comprising monoclonal antibody, modified antibody, derivative of antibody and fragment of antibody or any combination thereof.

In still another embodiment of the present disclosure, the heterogeneity is due to proportion of charge variant of the antibody; and wherein the reduction in the heterogeneity is carried out by reducing the proportion of Lysine residue on C-terminal of the antibody.

In still another embodiment of the present disclosure, the heterogeneity is reduced by carrying out the said method for proportion of antibodies ranging from about 75% to about 100%.

In still another embodiment of the present disclosure, the heterogeneity is reduced by decreasing basic variant proportion of the antibody from about 3% to about 30% and increasing main peak/0 Lysine from about 5% to about 25%.

In still another embodiment of the present disclosure, the culturing is fed batch culturing; and comprises mammalian cell culturing, preferably chinese hamster ovary (CHO) cell line culturing.

In still another embodiment of the present disclosure, the metal ion is $Zn^{+2}$, at a concentration ranging from about 0.05 mM to about 1.5 mM.

In still another embodiment of the present disclosure, the osmolality of the culture medium is altered to provide osmolality ranging from about 240 mOsm/Kg to about 260 mOsm/Kg.

In still another embodiment of the present disclosure, the addition of metal ion is carried out firstly during cell growth phase and secondly during polypeptide production phase of the culturing at temperatures ranging from about of about 30° C. to about 32° C., or wherein the addition of the metal ion is carried out at an initial phase before said culturing of the cells.

In still another embodiment of the present disclosure, the cell growth phase has a concentration of cells ranging from about $12 \times 10^6$ cells/ml to about $13 \times 10^6$ cells/ml, and wherein the polypeptide production phase has a concentration of cells ranging from about $13 \times 10^6$ cells/ml cells/ml to about $15 \times 10^6$ cells/ml cells/ml.

In an embodiment of the present disclosure the divalent zinc ions are used preferably in the form of Zinc Sulphate hepta hydrate. Other Zinc compounds may include, but not limited to $ZnH_2$, $Zn(OH)_2$, $Zn(NO_3)_2.6H_2O$ and $ZnCl_2$.

In an embodiment of the present disclosure the reduction in the heterogeneity is carried out by reducing the proportion of Lysine residue on C-terminal of the antibody without the use of an enzyme to remove the lysine residues. The present disclosure overcomes the limitations of prior art to provide for a method for reducing the heterogeneity of antibodies. It is an objective of the present disclosure to provide methods for improving protein production, e.g., large-scale commercial protein production, e.g., antibody production, utilizing a modified cell culture method comprising a cell growth phase and a polypeptide production phase.

In another objective of the present disclosure, the basic variant of the antibodies is decreased, by addition of metal ions like $Zinc^{+2}$.

In still another objective of the disclosure, the concentration of zinc ions is in the range from 0.05-1.5 mM.

In still another objective of the present disclosure, the basic variants of the antibodies are decreased by lowering the osmolality of the production media.

Still another objective of the present disclosure comprises method of growing cells in a cell culture system that decreases heterogeneity among charge variants by increasing the formation of main peak/0 Lysine, wherein there is essentially zero lysines on the C-terminus of any chains of the antibody.

Still another objective of the present disclosure basic variant in cell culture medium is decreased by 3-30%.

Accordingly present disclosure provides methods of improving protein production, e.g., large-scale commercial protein production, e.g., antibody production, utilizing a modified cell culture method comprising a cell growth phase and a polypeptide production phase.

Further disclosure states reducing microheterogeneity in antibodies. More specifically the disclosure comprises method of growing cells in a cell culture system that decreases heterogeneity among charge variants by decreasing the formation of Basic variants.

The present disclosure relates to a process for the production of a monoclonal antibody with an altered proportion of basic variants by culturing mammalian cells and isolating the MAb from the culture medium or/and the cells.

In an embodiment of the present disclosure, the basic variants of the antibodies is decreased, by addition of metal ions like $Zinc^{+2}$ in the range from 0.05-1.5 mM and by using the production media of osmolality range of 240-260 mOsm/Kg.

Yet another embodiment of the present disclosure decreases the % of basic variants of an antibody that are normally associated with standard production procedure. Advantageously the disclosure provides economic and commercial benefits through the recovery of the greater quantity of the product with desired quality especially for biosimilar antibodies.

Definition of the Terms

The term "antibody" includes antibodies or antibody derivatives or fragments thereof and the specifications of the antibodies also apply to the antibody preparation of the present disclosure. Among the antibody fragments functional equivalents or homologues of antibodies including any polypeptide comprise an immunoglobulin binding domain or peptides mimicking this binding domain together with a Fc region or a region homologous to a Fc region or at least part of it. Chimeric molecules comprising an immunoglobulin binding domain, or equivalents, fused to another polypeptide are included.

Exemplary antibody molecules are intact immunoglobulin molecules and those portions of an immunoglobulin molecule that contains the paratope, including those portions known as Fab, Fab', F(ab')2 ,Fc and F(v), as well as the N-glycan structure.

Antibody describes a functional component of serum and is often referred to either as a collection of molecules (antibodies or immunoglobulins, fragments, etc.) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or on distinct, different antigens). The distinct and different antibody molecules constituting a polyclonal antibody may be termed "members". Each antibody molecule has a unique structure that enables it to bind specifically to its corresponding antigen, and all natural antibody molecules have the same overall basic structure of two identical light chains and two identical heavy chains.

Heterogeneity is defined as a phenomena wherein secreted antibodies have various discrete biochemical forms, such as, but not limited to, an extra amino acid or acids on the carboxy terminus of one or both of the antibody heavy chains or as a modification in an amino acid which causes difference in the overall charge distribution of the antibody.

As used herein, the phrases "polypeptide" or "polypeptide product" are synonymous with the terms "protein" and "protein product," respectively, and, as is generally understood in the art, refer to at least one chain of amino acids linked via sequential peptide bonds. In certain embodiments, a "protein of interest" or a "polypeptide of interest" or the like is a protein encoded by an exogenous nucleic acid molecule that has been transformed into a host cell. In certain embodiments, wherein an exogenous DNA with which the host cell has been transformed codes for the "protein of interest," the nucleic acid sequence of the exogenous DNA determines the sequence of amino acids. In certain embodiments, a "protein of interest" is a protein encoded by a nucleic acid molecule that is endogenous to the host cell. In certain embodiments, expression of such an endogenous protein of interest is altered by transfecting a host cell with an exogenous nucleic acid molecule that may, for example, contain one or more regulatory sequences and/or encode a protein that enhances expression of the protein of interest.

As used herein, "antibody variant" refers to an antibody which has an amino acid sequence which differs from the amino acid sequence of a parent antibody. Preferably, the antibody variant comprises a heavy chain variable domain or a light chain variable domain having an amino acid sequence which is not found in nature. Such variants necessarily have less than 100% sequence identity or similarity with the parent antibody. In a preferred embodiment, the antibody variant will have an amino acid sequence from about 75% to less than 100% amino acid sequence identity or similarity with the amino acid sequence of either the heavy or light chain variable domain of the parent antibody, more preferably from about 80% to less than 100%, more preferably from about 85% to less than 100%, more preferably from about 90% to less than 100%, and most preferably from about 95% to less than 100%. Identity or similarity with respect to this sequence is defined herein as the percentage of amino acid residues in the candidate sequence that are identical (i.e same residue) with the parent antibody residues, after aligning the sequences and introducing gaps, if necessary, to achieve the maximum percent sequence identity.

The terms "medium," "cell culture medium," and "culture medium" as used herein refer to a solution containing nutrients that nourish growing animal cells, e.g., mammalian cells, and can also refer to medium in combination with cells.(Typically commercially available media such as of culture media Hyclone CDM4NS0, Hyclone CDM4Mab, Invitrogen CDOptiCHO and Lonza Power CHO can be used).

The preferred mammalian hosts are CHO cells and preferred mode of fermentation is fed batch. Examples of other cell lines NS0 (Non Secreting) and BHK (Baby Hamster Kidney).

Methods and vectors for genetically engineering cells and/or cell lines to express a protein of interest are well known to those skilled in the art. Genetic engineering techniques include but are not limited to expression vectors, targeted homologous recombination and gene activation. Optionally, the proteins are expressed under the control of a heterologous control element such as, for example, a promoter that does not in nature direct the production of that polypeptide. For example, the promoter can be a strong viral promoter (e.g., CMV, SV40) that directs the expression of a mammalian polypeptide. The host cell may or may not normally produce the protein. For example, the host cell can be a CHO cell that has been genetically engineered to produce a protein, meaning that nucleic acid encoding the protein has been introduced into the CHO cell.

One skilled in the art will recognize at what temperature and/or concentration a particular cell line should be cultured. For example, most mammalian cells, e.g., CHO cells, grow well within the range of about 35° C. to 39° C., preferably at 37° C., whereas insect cells are typically cultured at 27° C.

In one embodiment of the disclosure, the protein produced using the method of the disclosure is an antibody or an antigen-binding fragment thereof. As used herein, the term "antibody" includes a protein comprising at least one and typically two, VH domains or portions thereof, and/or at least one, and typically two, VL domains or portions thereof. In certain embodiments, the antibody is a tetramer of two heavy immunoglobulin chains and two light immunoglobulin chains, wherein the heavy and light immunoglobulin chains are interconnected by, e.g., disulfide bonds. The antibodies, or a portion thereof, can be obtained from any origin, including but not limited to, rodent, primate (e.g., human and nonhuman primate), shark, etc., or they can be recombinantly produced, e.g., chimeric, humanized, and/or in vitro-generated, e.g., by methods well known to those of skill in the art.

In the preferred embodiment, the cell culture of the present disclosure is performed in a shake flask (30 ml working volume) and/or a bioreactor (1 L/50 L) and fed-batch mode is employed. In the fedbatch cultures the mammalian host cells and culture medium with an osmolality of 300-310 mOsm/Kg are supplied initially and nutrients (amino acids, glucose and vitamins) fed periodically. The production fermentation run starts with an initial cell count of $0.5$-$0.6 \times 10^6$ cells/ml at 37±1° C., the first 3-4 days are dedicated to grow the cells. Next step involves lowering the temperature to 31±1° C. degree and addition of zinc ions intermittently twice such that the total amount of addition comes up to 0.05-1.5 mM (one shot during the growth phase-$3^{rd}/4^{th}$ day and the other shot during the production phase-$6^{th}/7^{th}/8^{th}$ day). The preparation of antibodies following the embodiments of the present disclosure preferably at least 90%, preferably at least 95%, more preferred at least 99%, most preferred 100% of the modified antibodies, derivatives or fragments thereof lack a C-terminal lysine residue, in particular determined on the sum of the heavy chains (which normally can comprise lysine). Since antibodies can have more chains which potentially comprise the C-terminal lysine it is understood that the quantitative percentage of the lack of lysine refers to all chains which potentially have the C-terminal lysine. It is shown that monoclonal antibodies are heterogeneous in the presence of the C-terminal lysine.

In another embodiment, the cell culture of the present disclosure is performed in a shake flask (30 ml working volume) and/or a bioreactor (1 L/50 L), and fedbatch mode is employed. In the preferred fedbatch cultures, the mammalian host cells and culture medium with a reduced osmolality of 240-260 mOsm/Kg are supplied initially, and nutrients (amino acids, glucose and vitamins) fed periodically. Osmolality of the medium is reduced by diluting the media with MilliQ/WFI. The production fermentation run starts with an initial cell count of $0.5$-$0.6 \times 10^6$ cells/ml at 37±1° C., the first 3-4 days are dedicated to grow the cells. Next step involves lowering the temperature to 31±1° C. and addition of zinc ions in the concentration of 0.1 mM intermittently twice (one shot during the growth phase-3rd/4th day and the other shot during the production phase-5th/6th/7th/8th day). The preparation of antibodies following the embodiments of the present disclosure preferably at least 90%, preferably at least 95%, more preferred at least 99%, most preferred 100% of the modified antibodies, derivatives or fragments thereof lack a C-terminal lysine residue, in particular determined on the sum of the heavy chains (which normally can comprise lysine). Since antibodies can have more chains which potentially comprise the C-terminal lysine it is understood that the quantitative percentage of the lack of lysine refers to all chains which potentially have the C-terminal lysine. It is shown that monoclonal antibodies are heterogeneous in the presence of the C-terminal lysine.

The foregoing descriptions of specific embodiments of the present disclosure are presented for purposes of illustration and description. They are not intended to be exhaustive or to limit the disclosure to the precise forms disclosed. Various modifications and variations are possible in view of the above teachings. In addition, many modifications may be made to adapt a particular situation, material, composition of matter, process, process step or steps, to the objective, spirit and scope of the present disclosure. All such modifications are intended to be within the scope of the claims appended hereto.

The technology of the instant Application is further elaborated with the help of following examples. However, the examples should not be construed to limit the scope of the disclosure.

EXAMPLES

The present disclosure discloses the production of antibodies with reduced heterogeneity. Antibody-1 is a humanized monoclonal antibody that inhibits vascular endothelial growth factor A (VEGF-A). Antibody-2 is a monoclonal antibody that interferes with the HER2/neu receptor (Anti her 2 antibody). Antibody-3 is a humanized monoclonal antibody that inhibits TNF and Antibody 4—is Anti CD6.

Example 1

Use of Zinc Ions to Decrease Basic Variants or Increase the Main Peak/0 Lysine of Antibody-1

Figure 1:
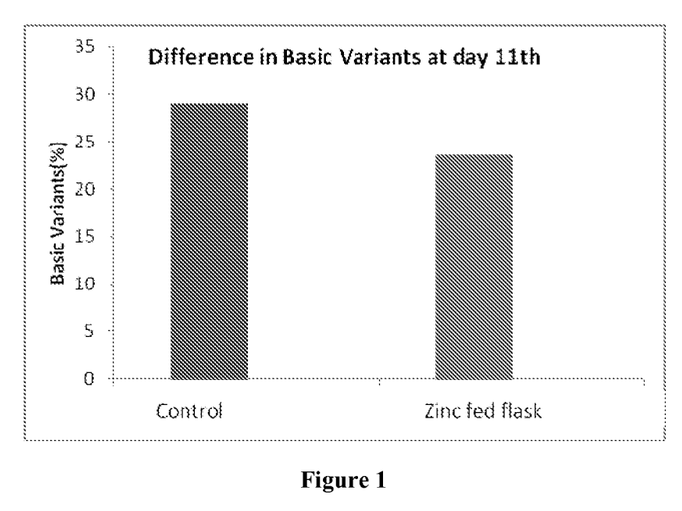
FIG. 1 shows the difference in the % of basic variants in the presence and absence of Zinc ions at 264 h i.e. day 11 (Antibody 1).

The culture media with osmolality of 300-310 mOsm/kg was supplied and inoculated with cells at a concentration of $0.5$-$0.6 \times 10^6$/ml and was allowed to grow. Once the cell count reached $12$-$13 \times 10^6$/ml on $4^{th}$ day, the temperature was shifted from 37° C. to 31° C. The first shot of Zinc was fed at a concentration of 0.1 mM. On the $8^{th}$ day, another shot of zinc was fed at concentration of 0.1 mM and when the cell count was $13$-$15 \times 10^6$/ml. It was allowed to run till $11^{th}$ day. The observed heterogeneity is tabulated as below.

TABLE 1

| Trial | Culture Day | 0 Lysine (%) | Basic (L1 + L2) % | Zn feeding (day) |
|---|---|---|---|---|
| Control | Day 11th | 55 | 27.8 | |
| Zn fed flask | | 60.9 | 24.1 | $4^{th}$ & $8^{th}$ day |

FIG. 1 illustrates the above results.

Example 2

Use of Zinc Ions to Decrease Basic Variants or Increase the Main Peak/0 Lysine of Antibody 1

Figure 2A:
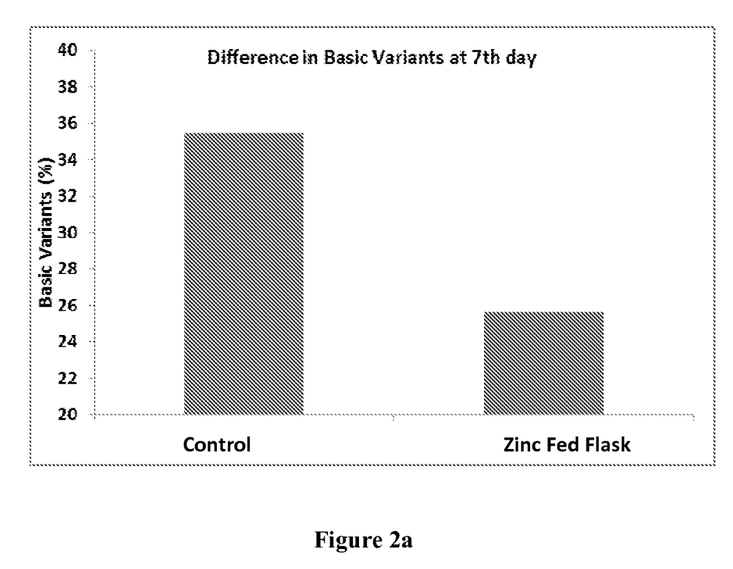
FIG. 2a shows the difference in the % of basic variants in the presence and absence of Zinc ions at 168 h i.e. day 7 (Antibody 1).
Figure 2B:
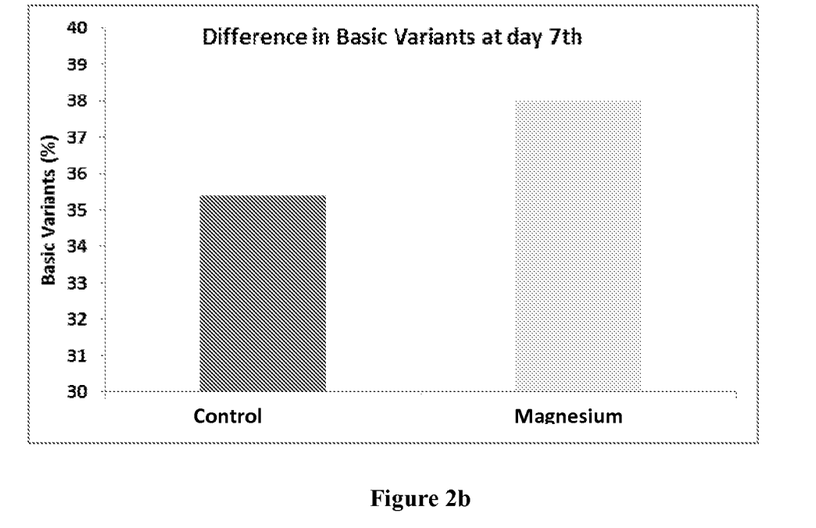
FIG. 2b shows the difference in the % of basic variants in the presence and absence of Magnesium ions at 168 h i.e. day 7 (Antibody 1).

Cell culture was performed in a fed batch mode. In the fed-batch cultures the mammalian host cells and culture medium were supplied initially and nutrients were fed periodically. The culture media was inoculated with cells at a concentration of 0.5-0.6×10$^6$/ml and was allowed to grow. Once the cell count reached 12-13×10$^6$/ml (at day 3rd), the temperature was shifted from 37° C. to 31° C. and then the first shot of Zinc ions was fed at a concentration of 0.1 mM. Another shot was fed when the cell count reached 13-15×10$^6$/ml (at day 6th) at a concentration of 0.1 mM and the flask was allowed to run till day 7th. In another Culture medium, magnesium ions were fed which showed no difference to basic variants and this example has been given as negative control. The observed heterogeneity is tabulated as below:

TABLE 2

| Trial | Culture Day | 0 Lysine (%) | Basic (L1 + L2) % | Zn feeding (day) |
|---|---|---|---|---|
| Control | Day 7th | 56.2 | 35.4 | |
| Zn fed flask | | 64.3 | 25.6 | Day 3$^{rd}$ & day 6th |
| Mg fed flask | | 46.1 | 38 | |

FIG. 2 illustrates the above results.

Example 3

Use of Low Osmolality Production Media with Zinc Ions to Decrease Basic Variants or Increase the Main Peak/0 Lysine of Antibody 1

Figure 3:
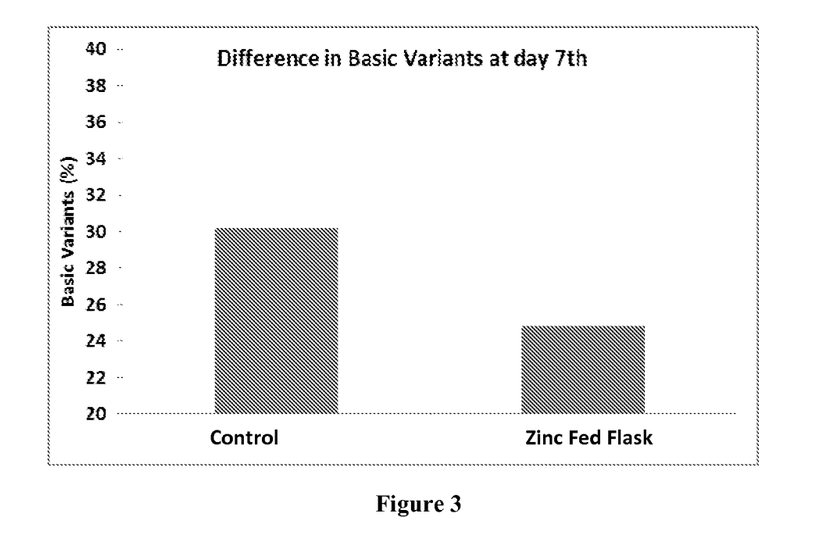
FIG. 3 shows the difference in the % of basic variants in the Low osmolality (240-260 mOsm/Kg) medium with Zinc ions and production medium of osmolality of 310-320 mOsm/Kg at 168 h i.e. day 7 (Antibody 1).

Cell culture was performed in a fed batch mode. In the cultures, the mammalian host cells and low osmolality culture medium were supplied initially and nutrients were fed periodically. The culture media was inoculated with cells at 0.5-0.6×10$^6$/ml and was allowed to grow. Once the cell count reached 12-13×10$^6$/ml (at day 3rd), the temperature was shifted from 37° C. to 31° C. and then first shot of Zinc ions was fed at a concentration of 0.1 mM. Another shot was fed when the cell count reached 13-15×10$^6$/ml (at day 6th) at a concentration of 0.1 mM and the fermentation was allowed to run till day 7th.

The observed osmolality is tabulated as below

TABLE 3

| Trial | Culture Day | 0 Lysine (%) | Basic (L1 + L2) % | Osmolality Range (mOsm/Kg) | Zn feeding (day) |
|---|---|---|---|---|---|
| High Osmolality (Control) | Day 7th | 50.9 | 30.2 | 300-360 | |
| Low Osmolality with Zinc ions | | 55.8 | 24.8 | 230-270 | Day 3$^{rd}$ & 6th |

FIG. 3 illustrates the above results.

Example 4

Use of Zinc Ions to Decrease Basic Variants or Increase the Main Peak/0 Lysine of Antibody 2

Figure 4:
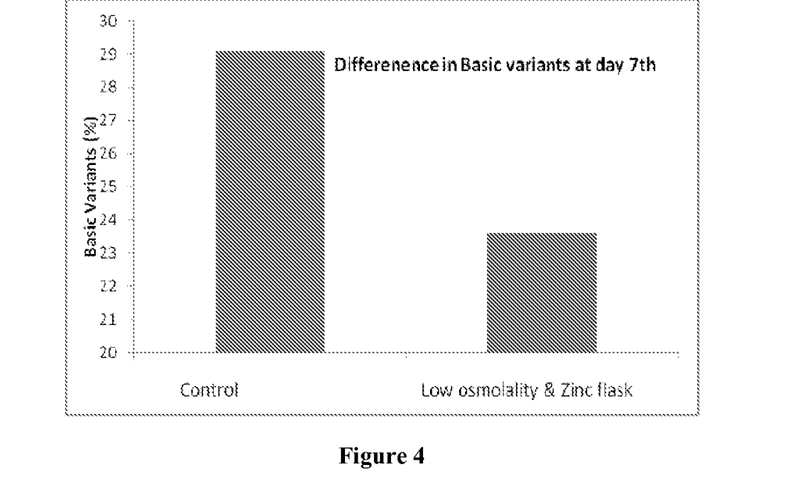
FIG. 4 shows the difference in the % of basic variants in the presence and absence of Zinc ions at 168 h i.e. day 7 (Antibody 2).

Cell culture was performed in fed batch mode. The cultures of the mammalian host cells and culture medium (with low osmolality) were supplied initially and nutrients were fed periodically. The culture media was inoculated with cells at 0.5-0.6×10$^6$/ml and allowed to grow. Once the cell count reached 12-13×10$^6$/ml (at day 3rd), the temperature was shifted from 37° C. to 31° C. and then the first shot of Zinc ions was fed at a concentration of 0.1 mM. Another shot was added when the cell count reaches 13-15×10$^6$/ml (at day 6th) at a concentration of 0.1 mM and the fermentation was allowed to run till day 7th. The observed heterogeneity is tabulated as below

TABLE 4

| Trial | Culture day | 0 Lysine (%) | Basic (L1 + L2) % | Zn feeding (day) |
|---|---|---|---|---|
| Control | Day 7th | 49.4 | 29.1 | |
| Zn fed flask | | 55 | 23.6 | Day 3$^{rd}$ & 6th |

FIG. 4 illustrates the above results.

Example 5

Use of Low Osmolality Production Media to Decrease Basic Variants or Increase the Main Peak/0 Lysine of Antibody 3

Figure 5:
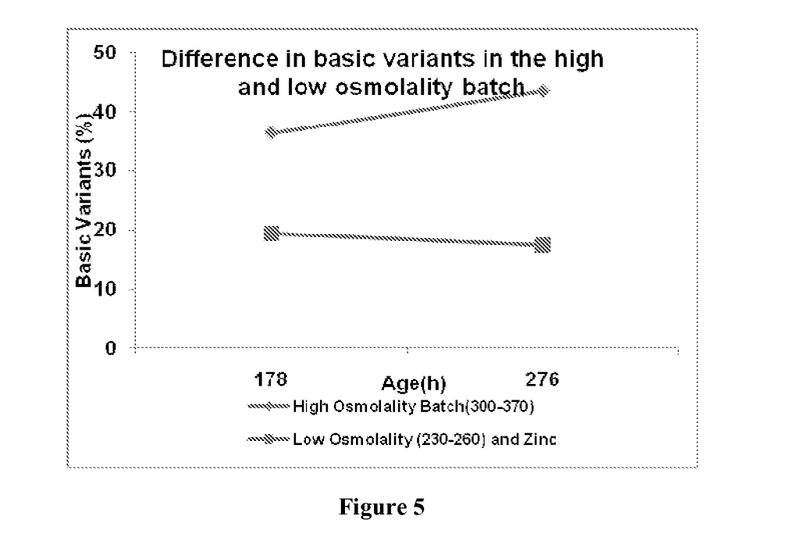
FIG. 5 shows the difference in the % of basic variants in the Low osmolality (240-260 mOsm/Kg) medium with Zinc ions and production medium of osmolality range (310-320 mOsm/Kg) (Antibody 3)

Cell culture is performed in a large scale bioreactor and fed batch mode was employed. In the fed-batch cultures the mammalian host cells and low osmolality culture medium were supplied initially and nutrients were fed periodically. In this trial the bioreactor was inoculated with cells at 0.5-0.6×10$^6$/ml and was allowed to grow. Once the cell count reached 12-13×10$^6$/ml (at day 3rd), the temperature was shifted from 37° C. to 31° C. and then the first shot of Zinc ions was fed at a concentration of 0.1 mM. Another shot was fed when the cell count reached 13-15×10$^6$/ml (at day 5th) at a concentration of 0.1 mM and the fermentation was allowed to run till day 12th.

The observed osmolality is tabulated as below

TABLE 5

| Trial | Culture Day | 0 Lysine (%) | Basic Variants (%) | Osmolality Range (mOsm/Kg) | Zn feeding (day) |
|---|---|---|---|---|---|
| Control batch | Day 8th | 47.8 | 36.2 | 300-370 | |
| | Day 12th | 36.2 | 43.2 | | |
| Low osmolality with zinc ions batch | Day 8th | 62.2 | 19.3 | 230-260 | Day 3$^{rd}$ & 5th |
| | Day 12th | 58.8 | 17.3 | | |

FIG. 5 illustrates the above results.

Example 6

Use of Low Osmolality Production Media to Decrease Basic Variants or Increase the Main Peak/0 Lysine of Antibody 1

Figure 6:
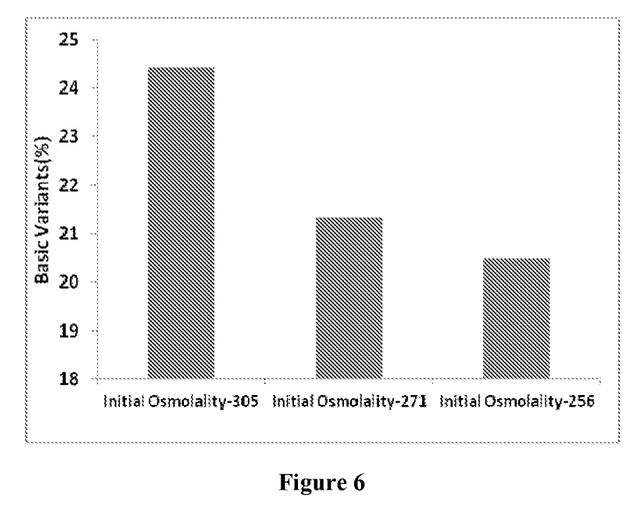
FIG. 6 shows the difference in the % of total Basic variants with different initial osmolality of the medium. (Antibody 1)

Cell culture was performed in a fed batch mode. In the fed-batch cultures the mammalian host cells and low osmolality culture medium were supplied initially and nutrients were fed periodically. Three media with different levels of initial osmolality were used. The culture media was inoculated with cells at 0.5-0.6×10⁶/ml and was allowed to grow. The batch was allowed to run till day 7th. Culture media show that with decrease in osmolality of the initial medium there is a decrease in the overall % of basic variants. There was no difference seen in the growth profile of the cell line. The Observed decrease in basic variants with decrease in Osmolality is tabulated as below.

TABLE 6

| Trial | Culture day | 0 Lysine (%) | Basic (L1 + L2) % | Initial Osmolality of the medium |
|---|---|---|---|---|
| Osmolality Trial | Day 8th | 41.1 | 24.4 | 305 |
| | | 42.9 | 21.3 | 271 |
| | | 45.2 | 20.5 | 256 |

FIG. 6 illustrates the above results.

Example 7

Use of Zinc Ions to Decrease Basic Variants or Increase the Main Peak/0 Lysine of Antibody 1

Figure 7:
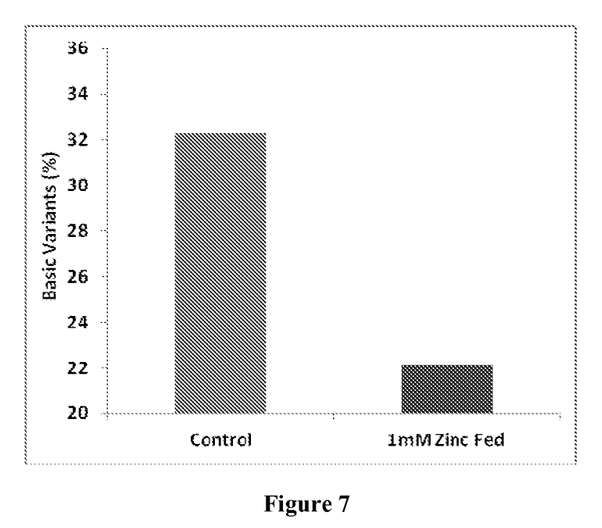
FIG. 7 shows the difference in the % of basic variants in the presence and absence of Zinc ions (1 mM) at 168 h i.e. day 7 (Antibody 1).

The cell culture was performed in fed batch mode. In the fed-batch cultures the mammalian host cells and culture medium were supplied initially (including 1 mM Zinc ions) and nutrients were fed periodically. The culture Media was inoculated with cells at 0.5-0.6×10⁶/ml and was allowed to grow. Once the cell count reached 12-13×10⁶/ml temperature was shifted from 37° C. to 31° C. and the flask was allowed to run till day 7th. The Observed reduction of heterogeneity is tabulated as below.

TABLE 7

| Trial | Culture Day | 0 Lysine (%) | Basic (L1 + L2) % |
|---|---|---|---|
| Control | Day 7th | 50.6 | 32.3 |
| 1 mM Zinc ions | | 57.9 | 22.1 |

FIG. 7 illustrates the above results.

Example 8

Use of Zinc Ions to Decrease Basic Variants or Increase the Main Peak/0 Lysine of Antibody 1

Figure 8:
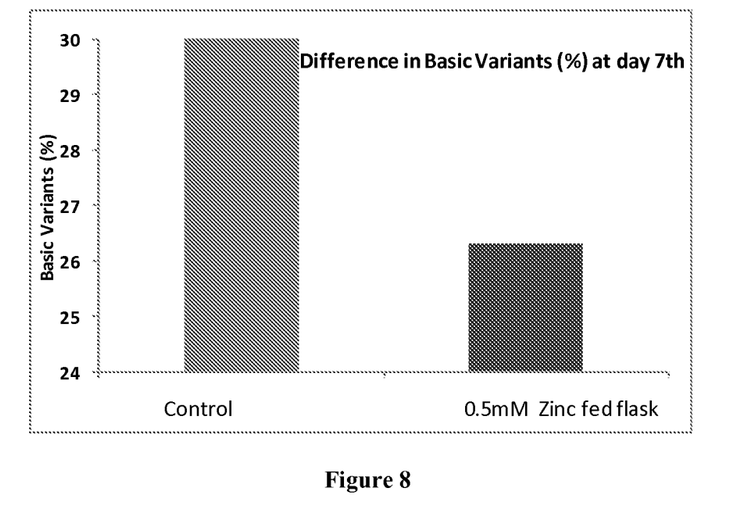
FIG. 8 shows the difference in the % of basic variants in the presence and absence of Zinc ions (0.5 mM) at 168 h i.e. day 7 (Antibody 1).

Cell culture was performed in a fed batch mode. The culture media with 0.5 mM of Zinc ions was inoculated with 0.5-0.6×10⁶/m10 cell and the culture was fed with nutrients periodically. Upon reaching cell count 12-13×10⁶/ml, the temperature was shifted to 31° C. and fermentation was allowed to run till day 7th. The Observed reduction of heterogeneity is tabulated as below.

TABLE 8

| Trial | Culture Day | 0 Lysine (%) | Basic (L1 + L2) % |
|---|---|---|---|
| Control | 7$^{th}$ | 46 | 30.4 |
| 0.5 mM Zinc ions | | 50.5 | 26.3 |

FIG. 8 illustrates the above results.

Example 9

Use of Zinc Ions to Decrease Basic Variants or Increase the Main Peak/0 Lysine of Antibody-3

Figure 9:
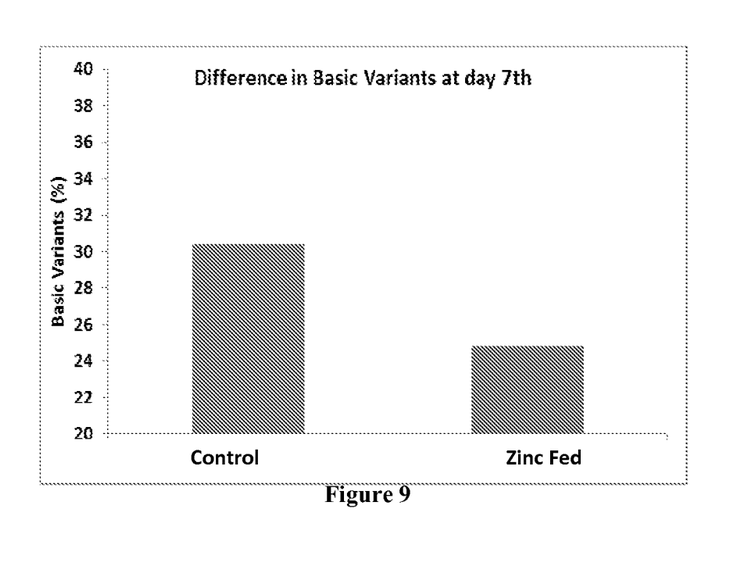
FIG. 9 shows the difference in the % of basic variants in the presence and absence of Zinc ions at 168 h i.e. day 7 (Antibody 3).

Cell culture was performed in employing fed batch mode. The culture media was inoculated with 0.5-0.6×10⁶/ml and allowed to grow. Upon reaching cell count of 12-13×10⁶/ml the temperature was shifted from 37° C. to 31° C. and first shot of Zinc ion at concentration of 0.1 mM was fed and other shot was fed at 6th day and allowed to run till 7$^{th}$ day. The observed heterogeneity is tabulated as below

TABLE 9

| Trial | Age (h) | 0 Lysine (%) | Basic (L1 + L2) % | Zn feeding (Number of days of culture) |
|---|---|---|---|---|
| Control | 168 | 55.9 | 30.4 | |
| Zn fed flask | 168 | 60.5 | 23.3 | 3$^{rd}$ & 6$^{th}$ day |

FIG. 9 illustrates the above results.

Example 10

Use of Zinc Ions to Decrease Basic Variants or Increase the Main Peak/0 Lysine of Antibody-4

Figure 10:
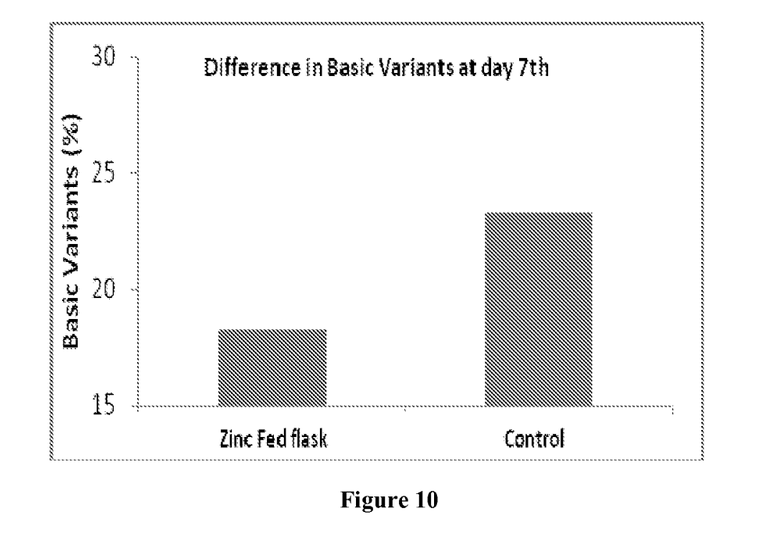
FIG. 10 shows the difference in the % of basic variants in the presence and absence of Zinc ions at 168 h i.e. day 7 (Antibody 4).

Cell culture was performed in fed batch mode. In the fed-batch cultures the mammalian host cells and culture medium were supplied initially and nutrients were fed periodically. The culture media was inoculated with cells at a concentration of 0.5-0.6×10⁶/ml and was allowed to grow. Once the cell count reached 12-13×10⁶/ml (at day 3rd), the temperature was shifted from 37° C. to 31° C. and first shot of Zinc ions was fed at a concentration of 0.1 mM, followed by another shot is when the cell count reached 13-15×10⁶/ml (at day 6th) at a concentration of 0.1 mM and the fermentation was allowed to run till day 7$^{th}$. The Observed reduction of heterogeneity is tabulated as below.

TABLE 10

| Trial | Age (h) | 0 Lysine (%) | Basic (L1 + L2) % | Zn feeding (Number of days of culture) |
|---|---|---|---|---|
| Control | 168 | 58.9 | 23.3 | |
| Zn fed flask | 168 | 64.5 | 18.3 | 3$^{rd}$ & 6$^{th}$ day |

FIG. 10 illustrates the above results.

Example 11

Use of Zinc Ions to Decrease Basic Variants or Increase the Main Peak/0 Lysine of Antibody-1

Figure 11:
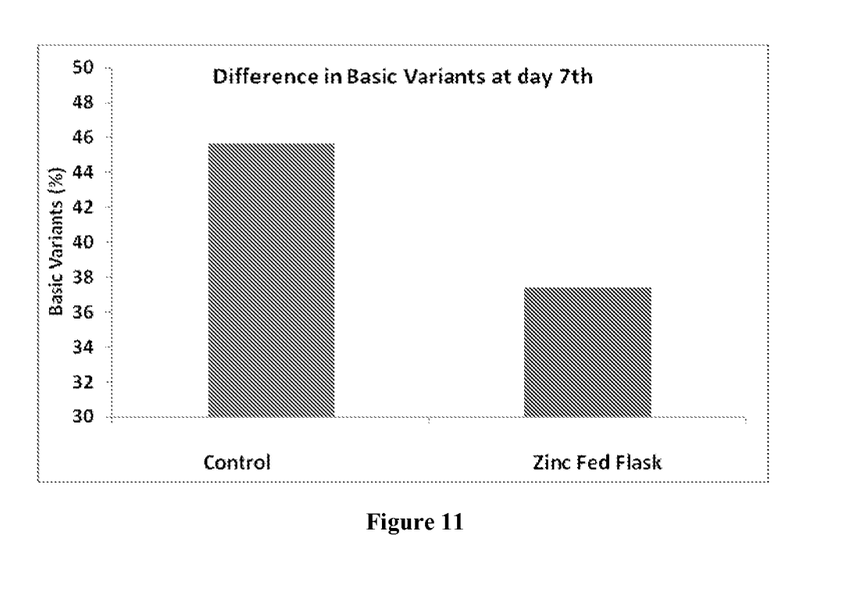
FIG. 11 shows the difference in the % of basic variants in the presence and absence of Zinc ions at 168 h i.e. day 7 (Antibody 1).

Cell culture was performed in fed batch mode. Hyclone CDM4Mab culture medium was periodically fed with nutrients. The culture media was inoculated with cells at 0.5-0.6×10⁶/ml and was allowed to grow. Once the cell count reached 12-13×10⁶/ml (day), the temperature was shifted from 37° C. to 31° C. and then the first shot of Zinc ions was fed at a concentration of 0.15 mM and was followed by another shot at day 6$^{th}$ and the fermentation was allowed to run till day 7. The observed reduction of heterogeneity is tabulated as below:

TABLE 11

| Trial | Age (h) | 0 Lysine (%) | Basic (L1 + L2) % | Zn feeding (Number of days of culture) |
|---|---|---|---|---|
| Control | 168 | 40.7 | 45.6 | |
| Zn fed flask | 168 | 46.3 | 37.4 | 3$^{rd}$ & 6$^{th}$ day |

FIG. 11 illustrates the above results

Example 12

Use of Zinc Ions to Decrease Basic Variants or Increase the Main Peak/0 Lysine of Antibody-3

Figure 12:
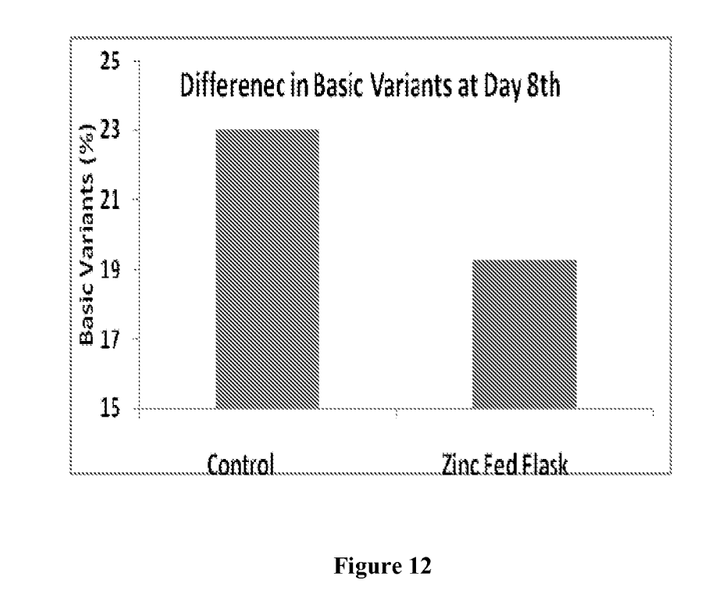
FIG. 12 shows the difference in the % of basic variants in the presence and absence of Zinc ions at 192 h i.e. day 8 (Antibody 3).

Cell culture was performed in fed batch mode. Invitrogen CDOptiCHO culture media was periodically supplied with nutrients. The culture media was inoculated with cells at 0.5-0.6×10$^6$/ml and was allowed to grow. Once the cell count reached 12-13×10$^6$/ml (day 3) the temperature was shifted from 37° C. to 31° C. and a first shot of Zinc ions was fed at a concentration of 0.1 mM, followed by another shot at day 6 and the fermentation was allowed to run till day 8. The observed reduction of heterogeneity is tabulated as below:

TABLE 12

| Trial | Age (h) | 0 Lysine (%) | Basic (L1 + L2) % | Zn feeding (Number of days of culture) |
|---|---|---|---|---|
| Control | 192 | 61.5 | 23 | |
| Zn fed flask | 192 | 65.6 | 19.2 | 3$^{rd}$ & 6$^{th}$ day |

FIG. 12 illustrates the above results

We claim:

1. A method of reducing heterogeneity in antibodies obtained by cell culturing by reducing the proportion of lysine residue on C-terminal of the antibodies, said method comprises adding a divalent transitional metal ion at a concentration ranging from 0.05 mM to 5 mM to the antibody producing culture medium or altering osmolality of the culture medium or a combination thereof to obtain said antibodies with reduced heterogeneity wherein the osmolality of the culture medium is reduced to provide osmolality ranging from 240 mOsm/Kg to 260 mOsm/Kg, wherein the cells are Chinese Hamster Ovary (CHO) cells.

2. The method as claimed in claim 1, wherein the heterogeneity is due to proportion of charge variant of the antibody.

3. The method as claimed in claim 1, wherein the heterogeneity is reduced by carrying out the said method for proportion of antibodies ranging from about 75% to about 100%.

4. The method as claimed in claim 1, wherein the antibody is a naturally occurring antibody or a recombinant antibody selected from a group comprising monoclonal antibody, modified antibody, derivative of antibody and fragment of antibody or any combination thereof.

5. The method as claimed in claim 2, wherein the reduction in heterogeneity of basic variant proportion of the antibody is from 3% to 30% and increase of main peak/0 Lysine of antibody is from 5% to 25%.

6. The method as claimed in claim 1, wherein the metal ion is $Zn^{+2}$.

7. The method as claimed in claim 1, wherein the culturing is fed batch culturing; and comprises mammalian cell culturing.

8. The method as claimed in claim 1, wherein the addition of the divalent transitional metal ions is carried out firstly during cell growth phase and secondly during polypeptide production phase of the cell culturing; or wherein the addition of the metal ion is carried out at an initial phase before said culturing of the cells.

9. A process for producing antibody having reduced heterogeneity by reducing the proportion of lysine residue on C-terminal of the antibody, said process comprising acts of:
  a) culturing cells in culture medium for producing the antibody, and adding divalent transitional metal ions at a concentration ranging from 0.05 mM to 1.5 mM to the culture medium or altering osmolality of the culture medium or a combination thereof, wherein the osmoiality of the culture medium is reduced to provide osmolality ranging from 240 mOsm/Kg to 260 mOsm/Kg; and
  b) recovering the antibody from the culture medium having the reduced heterogeneity.

10. The process as claimed in claim 9 (a), wherein the cells are cultured at a concentration ranging from about 0.5×10$^6$ cells/ml to about 0.6×10$^6$ cells/ml.

11. The process as claimed in claim 9 (a), wherein the culturing is carried out at temperatures ranging from about 36°C. to about 38° C.

12. The process as claimed in claim 10, wherein the antibody is a naturally occurring antibody or a recombinant antibody selected from a group comprising monoclonal antibody, modified antibody, derivative of antibody and fragment of antibody or any combination thereof.

13. The process as claimed in claim 9, In the heterogeneity is due to proportion of charge variant of the antibody.

14. The process as claimed in claim 9, wherein the heterogeneity is reduced by carrying out the said method for proportion of antibodies ranging from about 75% to about 100%.

15. The method as claimed in claim 13, wherein the reduction in heterogeneity of basic variant proportion of the antibody is from 3% to 30% and increase of main peak/0 Lysine of antibody is from 5% to 25%.

16. The process as claimed in claim 9, wherein the culturing is fed batch culturing; and comprises mammalian cell culturing.

17. The process as claimed in claim 9, wherein the metal ion is $Zn^{+2}$.

18. The process as claimed in claim 9, wherein the addition of the divalent transitional metal ions is carried out firstly during cell growth phase and secondly during polypeptide production phase of the culturing at temperatures ranging from about of about 30 ° C. to about 32° C.; or wherein the addition of the metal divalent transitional ions is carried out at an initial phase before said culturing of the cells.

19. The process as claimed in claim 18, wherein the cell growth phase has a concentration of cells ranging from about 12×10$^6$ cells/ml to about 13×10$^6$ cells/ml; and wherein the polypeptide production phase has a concentration of cells ranging from about 13×10$^6$ cells/ml cells/ml to about 15×10$^6$ cells/ml.

* * * * *